United States Patent
Harrison et al.

(10) Patent No.: US 10,301,938 B2
(45) Date of Patent: *May 28, 2019

(54) MICROFLUIDIC OSCILLATING TUBE DENSITOMETER FOR DOWNHOLE APPLICATIONS

(71) Applicant: SCHLUMBERGER TECHNOLOGY CORPORATION, Sugar Land, TX (US)

(72) Inventors: Christopher Harrison, Newton, MA (US); Chloe Coleou, Clamart (FR); Bill Grant, Cedar Creek, TX (US); Jacques Jundt, Newton Highlands, MA (US)

(73) Assignee: SCHLUMBERGER TECHNOLOGY CORPORATION, Sugar Land, TX (US)

(*) Notice: Subject to any disclaimer, the term of this patent is extended or adjusted under 35 U.S.C. 154(b) by 856 days.

This patent is subject to a terminal disclaimer.

(21) Appl. No.: 14/821,318

(22) Filed: Aug. 7, 2015

(65) Prior Publication Data

US 2015/0345289 A1     Dec. 3, 2015

Related U.S. Application Data

(63) Continuation of application No. 12/493,717, filed on Jun. 29, 2009, now Pat. No. 9,341,059.

(Continued)

(51) Int. Cl.
*E21B 49/08* (2006.01)
*G01N 29/02* (2006.01)
(Continued)

(52) U.S. Cl.
CPC .......... *E21B 49/08* (2013.01); *G01N 9/002* (2013.01); *G01N 27/74* (2013.01); *G01N 29/02* (2013.01); *E21B 2049/085* (2013.01)

(58) Field of Classification Search
CPC .. E21B 2049/085; G01N 29/02; G01N 9/002; G01N 27/74

See application file for complete search history.

(56) References Cited

U.S. PATENT DOCUMENTS

| 3,728,893 A | 4/1973 | Janssen |
| 4,047,814 A | 9/1977 | Westcott |

(Continued)

FOREIGN PATENT DOCUMENTS

| EP | 0905504 A1 | 3/1999 |
| EP | 1698880 A1 | 9/2006 |

(Continued)

OTHER PUBLICATIONS

Albert et al., "High-precision flow densimeter for fluids at temperatures to 700 K and pressure to 40 MPa", Review of Scientific Instruments, Apr. 1984, vol. 55, No. 4, pp. 589-593.

(Continued)

*Primary Examiner* — Patrick Assouad
*Assistant Examiner* — Haidong Zhang
(74) *Attorney, Agent, or Firm* — Eileen Pape

(57) ABSTRACT

Devices, methods and systems for determining one or more properties of at least one fluid sample. A tube configured to receive the at least one fluid sample wherein the tube is placed in a pressure housing. Further, an excitation source configured to generate vibration of the tube whereby a circulation of an electrical current along a portion of the tube is subjected to at least one magnetic field produced by at least one magnet. Further still, at least one vibration sensor that converts vibrations of the tube into a measurement signal. Finally, a processor that receives the measurement signal determines a resonant frequency from the measure- (Continued)

ment signal using a frequency measuring device to determine a property of the one or more properties of the at least one sample fluid.

20 Claims, 5 Drawing Sheets

Related U.S. Application Data

(60) Provisional application No. 61/169,485, filed on Apr. 15, 2009.

(51) Int. Cl.
*G01N 27/74* (2006.01)
*G01N 9/00* (2006.01)

(56) References Cited

U.S. PATENT DOCUMENTS

| | | | |
|---|---|---|---|
| 4,170,128 A | 10/1979 | Kratky et al. | |
| 4,655,075 A | 4/1987 | Albert et al. | |
| 4,767,426 A * | 8/1988 | Daly | B01D 39/2024 156/86 |
| 4,777,833 A | 10/1988 | Carpenter | |
| 4,796,468 A | 1/1989 | Blake-Coleman et al. | |
| 4,951,749 A | 8/1990 | Carroll | |
| 5,009,109 A | 4/1991 | Kalotay et al. | |
| 5,230,254 A | 7/1993 | Craft | |
| 5,321,991 A * | 6/1994 | Kalotay | G01F 1/8422 73/861.357 |
| 5,473,949 A | 12/1995 | Cage et al. | |
| 5,477,726 A | 12/1995 | Stabinger et al. | |
| 5,901,788 A | 5/1999 | Brown et al. | |
| 6,378,364 B1 | 4/2002 | Pelletier et al. | |
| 6,513,393 B1 | 2/2003 | Eckert et al. | |
| 6,543,281 B2 | 4/2003 | Pelletier et al. | |
| 6,704,666 B2 | 3/2004 | Normen | |
| 6,910,366 B2 | 6/2005 | Drahm et al. | |
| 7,036,355 B2 | 5/2006 | Drahm et al. | |
| 7,114,562 B2 | 10/2006 | Fisseler et al. | |
| 7,194,902 B1 * | 3/2007 | Goodwin | E21B 49/10 73/152.24 |
| 7,222,671 B2 | 5/2007 | Caudwell et al. | |
| 7,263,882 B2 | 9/2007 | Sparks et al. | |
| 7,434,457 B2 | 10/2008 | Goodwin et al. | |
| 7,520,162 B2 | 4/2009 | Wenger et al. | |
| 7,549,319 B2 | 6/2009 | Headrick | |
| 7,575,681 B2 | 8/2009 | Angelescu et al. | |
| 7,958,772 B2 | 6/2011 | Permuy et al. | |
| 8,106,361 B2 | 1/2012 | Benes | |
| 2001/0039829 A1 | 11/2001 | Wenger et al. | |
| 2004/0123645 A1 * | 7/2004 | Storm, Jr. | G01F 1/8495 73/32 A |
| 2005/0028974 A1 | 2/2005 | Moody | |
| 2006/0008913 A1 * | 1/2006 | Angelescu | B01D 17/085 436/28 |
| 2008/0115577 A1 | 5/2008 | Headrick | |
| 2008/0218733 A1 | 9/2008 | Benes | |
| 2009/0064693 A1 | 3/2009 | Matsiev et al. | |
| 2010/0263862 A1 | 10/2010 | Goodwin | |

FOREIGN PATENT DOCUMENTS

| | | |
|---|---|---|
| EP | 1724558 A1 | 11/2006 |
| GB | 1189083 A | 4/1970 |
| GB | 2001759 A | 2/1979 |
| GB | 2099148 A | 12/1982 |
| GB | 2421573 A | 6/2006 |
| JP | S2134031 A | 8/1987 |
| JP | H05142134 A | 6/1993 |
| JP | H05215659 A | 8/1993 |
| JP | H06331406 A | 12/1994 |
| JP | S63017442 A | 2/1998 |
| JP | H10185646 A | 7/1998 |
| JP | 2004061124 A | 2/2004 |
| JP | 2006017520 A | 1/2006 |
| WO | WO8505677 A1 | 12/1985 |
| WO | WO8802853 A1 | 4/1988 |
| WO | WO9012306 A1 | 10/1990 |
| WO | WO0036379 A1 | 6/2000 |
| WO | WO2007130516 A2 | 11/2007 |

OTHER PUBLICATIONS

Ashcroft, S. J.; Booker, D. R.; Turner, J. C. R. "Density Measurements by Oscillating Tube Effects of Viscosity, Temperature, Calibration and Signal Processing", J. Chem. Soc. Faraday Trans. 1990, 86, 145-149.
Bernhardt, J.; Pauly, H. "Pycnometric vs. Densimetric Measurements of Highly Viscous Protein Solutions", J. Phys. Chem. 1980, 84, 158-162.
Blencoe et al, "A Vibrating-Tube Densimeter for Fluids at High Pressures and Temperatures", International Journal of Thermophysics, 17(1), 179-190 (1996).
Bouchot, D. Richon, An enhanced method to calibrate vibrating tube densimeters, Fluid Phase Equilibria 191 (2001) 189-208.
Camunas et al., "Density of Diethyl Adipate using a new vibrating tube densimeter from (293.15 to 403.15) K and up to 140 Mpa. Calibration and Measurements", J. Chem. Eng. Data, 2008, vol. 53: pp. 986-994.
Chang et al., High-Temperature High-Pressure oscillating tube densimeter, Rev. Sci. Instrum. 67, 251-256 (1996).
Enoksson, P.; Stemme, G.; Stemme, E. "Fluid Density Sensor based on resonance vibration", Sens. Act. A 1995, 46, 3275.
Fitzgerald, H. D.; Jones, G. An Assessment of Laboratory density meters. Pet. Rev. 1992, 46, 544-549.
Fujii et al., Absolute Density Standards Measurement of the Thermodynamic Properties of Single Phases, Ch. 5, Elsevier for International Union of Pure and Applied Chemistry: Amsterdam, 2003; pp. 191 to 208.
Fujii et al., Present state of the solid and liquid density standards. Metrologia 2004, 41, S1-S15.
Herrero-Alvarez et al., "Electronic circuit for sustaining the oscillations of a vibrating element: Application to density measurements", Review of Scientific Instruments, vol. 68, No. 10, pp. 3835-3838 (1997).
International preliminary report on patentability issued in the related PCT application PCT/US2010/030026, dated Oct. 18, 2011 (5 pages).
International Search Report and Written Opinion issued in the related PCT application PCT/US2010/030026, dated Nov. 26, 2010 (7 pages).
Kratky, O.; Leopold, H.; Stabinger, H. "Determination of Density of Liquids and gases to an Accuracy of 10-6g/cm3, with a smaple volume of only 0.6 cm3", Z. Angew. Phys. 1969, 27, 273-277, English Abstract only.
Kuramoto et al. Accurate density measurements of reference liquids by a magnetic suspension balance. Metrologia 2004, 41, S84-S94.
Lagourette, C. Boned, H. Saint-Guirons, P. Xans and H. Zhout, Densimeter Calibration Method versus temperature and pressure , Meas. Sci. Technol. 3, 699-703 (1992).
Laznickova and H. Huemer, Investigations on the limits of uncertainity of gas density measurements with vibrating tube densimeters, Meas. Sci. Technol. 9, 719-733 (1998).
Majer and Pàdua, Chapter 5.2.2: Vibrating-Tube Densimeters, Measurement of the Thermodynamic Properties of Single Phases, Ch. 5, Goodwin et al., Amsterdam, 2003; pp. 158-168.
McCain, Jr., Chapter 2: Phase Behaviour, The Properties of Petroleum Fluids, 2nd ed. (1990), pp. 46-89.
Mullins et al., "Compartment Identification by Downhole Fluid Analysis", Petrophysics 46, 302-312 (2005).
Stansfeld, "Chapter 5, Section 5.7: In Situ Density Measurements", Measurement of the Thermodynamic Properties of Single Phases, Ch. 5, Goodwin et al., Amsterdam, 2003; pp. 208-225.
Wagner and Kleinrahm "Densimeters for very accurate density measurements of fluids over large ranges of temperature, pressure,

(56) References Cited

OTHER PUBLICATIONS and density". Metrologia 2004, 41, S24-S39.

Wagner et al., Chapter 5: Density Measurement of the Thermodynamic Properties of Single Phases, Ch. 5, Goodwin et al., Amsterdam, 2003; pp. 127-235.

Examination Report issued in related CA Application No. 2,699,931 dated Jul. 16, 2013 (3 pages).

Examination Report issued in related CA Application No. 2,699,931 dated Feb. 24, 2014 (3 pages).

Notice of Allowance issued in related CA Application No. 2,699,931 dated Oct. 28, 2014 (1 page).

Examination Report issued in related CA Application No. 2,753,389 dated Nov. 14, 2013 (3 pages).

Examination Report issued in related CA Application No. 2,753,389 dated Oct. 30, 2014 (3 pages).

Notice of Allowance issued in related CA Application No. 2,753,389 dated Oct. 8, 2015 (1 page).

Office Action issued in related JP Application No. 2012-503776 dated Sep. 24, 2013, with English translation by agent (5 pages).

Notice of Allowance issued in related JP Application No. 2012-503776 dated Feb. 4, 2014 (4 pages).

\* cited by examiner

MICROFLUIDIC OSCILLATING TUBE DENSITOMETER FOR DOWNHOLE APPLICATIONS

RELATED APPLICATIONS

This patent application is a continuation application of U.S. patent application Ser. No. 12/493,717 (now U.S. Pat. No. 9,341,059), filed Jun. 29, 2009, which claims the benefit of U.S. application Ser. No. 61/169,485, filed Apr. 15, 2009, both of which are hereby incorporated by reference in their entireties.

BACKGROUND OF THE INVENTION

1. Field of the Invention

The present invention generally relates to devices and methods for measuring fluid properties for oilfield applications and other industries, e.g., chemical and food industries. In particular, the invention relates to the measurement of the density of microfluidic volumes of fluids for surface and downhole oilfield applications.

2. Background of the Invention

Understanding fluid density and other fluid properties downhole is paramount to petroleum exploration as it enables one to differentiate between oil, gas and water [W. D. McCain, Jr., *The Properties of Petroleum Fluids*, $2^{nd}$ ed. (1990)]. Furthermore, it allows one to locate the oil-water contact line and hence the thickness of the pay zone of a formation. As a consequence, it is a must that robust sensors be developed that can accurately measure fluid density and other fluid properties in a harsh environment found in an oilwell. Oilfield pressures downhole typically range as high as 15,000 psi with temperatures as high as 150° C., though wells exist with far more extreme conditions, especially offshore. A further challenge in downhole fluid analysis is that it is a challenge to obtain large quantities of representative downhole fluids due to the ever-present contamination, whether drilling mud or formation water [O. C. Mullins, M. Hashem, H. Elshahawi, G. Fujisawa, C. Dong, S. Betancourt, T. Terabayashi, Petrophysics 46, 302 (2005)]. Hence sensors that can operate with small quantities of fluid provide a great advantage. Further, Schlumberger has made some progress on miniaturizing vibrating tube densitometers as noted in J. G. Blencoe, S. E. Drummond, J. C. Seitz, and B. E. Nesbitt, International Journal of Thermophysics, 17, 179 (1996).

The vibrating tube densitometer has a well-deserved reputation as the world's most accurate technology for measuring fluid density among other things, both at ambient conditions and at elevated temperature and pressure [J. G. Blencoe, S. E. Drummond, J. C. Seitz, and B. E. Nesbitt, International Journal of Thermophysics, 17, 179 (1996) and R. Laznickova and H. Huemer, Meas. Sci. Technol. 9, 719-733 (1998)]. It is noted that the accuracy is in part due to the simplicity and the robustness of the underlying physics as well as its suitability to a wide range of temperature and pressure. For example, a measurement is performed by filling the tube with the fluid to be measured and the tube is excited at its resonant frequency by a piezoelectric or electromagnet actuator. Motion and hence the resonant frequency is measured with a piezoelectric transducer or an electric pickup coil. Adding the mass of such transducers decreases the sensor's sensitivity to fluid density as well as adding to the complexity of the device. Furthermore, the temperature dependence of these transducers must be incorporated into the interpretation.

Density of a single phase fluid can be one of the fundamental physical parameters required to describe fluid flow, either within the reservoir or borehole, as well as determine both the properties of the surface facilities and the economic value of the fluid as noted above; it is also required to provide the volume translation factor for cubic equations of state that are then used for reservoir simulator. A measure of the single phase fluid density within a sampling tool provides a real-time in situ determination of bore-hole fluid contamination as well as economic value. Immiscible fluids are required or a separator may be needed to provide the single phase fluid. Measurements with emulsions may be performed and it then becomes a matter of knowing the volume of each co-mingled phase before the density of the oil can be extracted; this can be achieved with, as an example, coincidence gamma-ray attenuation measurements with a micro Curie source as described by Schlumberger. For most applications outside of equation of stak analysis, an expanded uncertainty in density of $\pm 0.01 \cdot \rho$ can be sufficient.

Moreover, there are many methods that can be used to measure fluid density in a laboratory, for example some of these methods are described by the following: 1) Wagner et al. [J. W. Density in *Experimental Thermodynamics Vol. VI, Measurement of the Thermodynamic Properties of Single Phases*, Ch. 5, Goodwin, A. R. H., Marsh, K. N., Wakeham W. A. Eds.; Elsevier for International Union of Pure and Applied Chemistry: Amsterdam, 2003; pp 127-235]; 2) Wagner and Kleinrahm [Densimeters for very accurate density measurements of fluids over large ranges of temperature, pressure, and density. Metrologia 2004, 41, S24-S39]; and 3) Kuramoto et al. [Accurate density measurements of reference liquids by a magnetic suspension balance. Metrologia 2004, 41, S84-S94]. However, Fujii further describes absolute density standards [Absolute Density Standards in Experimental Thermodynamics Vol. VI, Measurement of the Thermodynamic Properties of Single Phases, Ch. 5, Goodwin, A. R. H., Marsh, K. N., Wakeham W. A. Eds.; Elsevier for International Union of Pure and Applied Chemistry: Amsterdam, 2003; pp 191 to 208, and Present state of the solid and liquid density standards. Metrologia 2004, 41, S1-5].

Of the above-mentioned methods, the methods that appear most appropriate for down-hole applications are those that do not rely on the knowledge of the orientation of the transducer with respect to the local gravitational field. These methods are based on determining the resonance frequency of a vibrating object and have been summarized by Majer and Pádua [Measurement of Density with Vibrating Bodies in Experimental Thermodynamics Vol. VI, Measurement of the Thermodynamic Properties of Single Phases, Ch. 5, Goodwin, A. R. H., Marsh, K. N., Wakeham W. A., Eds.; Elsevier for International Union of Pure and Applied Chemistry: Amsterdam, 2003; pp 158-168] and in particular Stansfeld with descriptions of devices for use at well-heads and pipelines [In situ Density Measurement in Experimental Thermodynamics Vol. VI, Measurement of the Thermodynamic Properties of Single Phases, Ch. 5, Goodwin, A. R. H., Marsh, K. N., Wakeham W. A., Eds.; Elsevier for International Union of Pure and Applied Chemistry: Amsterdam, 2003; pp 208-225].

There are many geometrical arrangements that have been reported for oscillating object densimeters with the fluid contacting either the outer or inner surface of, what is usually a metallic object. When the fluid is in contact with the outer surface, the measurement is usually considered intrusive when operated at elevated pressure, but when the fluid is inside the tube it is a non-invasive measurement.

Once the particular device has been selected it remains a task to develop a working equation, based on the principles of physics, that relates the measured quantity (in this case frequency) to density and provide a measurement with an expanded (k=2 or 95% confidence interval).

In view of tubulars used within a Modular Dynamics Tester (MDT) a measure of density may be best obtained by a vibrating tube. The vibrating U-tube is one of the plausible geometries, however there are others [In situ Density Measurement in Experimental Thermodynamics Vol. VI, Measurement of the Thermodynamic Properties of Single Phases, Ch. 5, Goodwin, A. R. H., Marsh, K. N., Wakeham W. A., Eds.; Elsevier for International Union of Pure and Applied Chemistry: Amsterdam, 2003; pp 208-225]. Tubes offer another advantage for wire-line (as well as other tool conveyance methods and MWD) in that they can be of low mass and be well suited to sustaining mechanical shock; rapid changes in local acceleration and the resultant application of large forces. Indeed, as the internal diameter of the tube decreases so does the outer diameter while still maintaining the ability to sustain a pressure difference across the tube from within. The type of material used to construct the tube and the elastic properties will determine the absolute value of the pressure difference sustainable by a tube wall.

Most densitometers are calibrated using a calibration fluid having a known density wherein the density is measured at a specified temperature. The problem with trying to obtain a density measurement outside of a laboratory/controlled environment is that the density of most fluids varies with temperature. Presently, many currently designed densitometers require that the temperature of the calibration fluid must be controlled prior to the fluid being injected into the densitometer for calibration. This means that the calibration fluid must be in a container that is temperature controlled so that the fluid will be held at a constant temperature. It is noted that the piping of the fluid from the container to the densitometer must also be temperature controlled to ensure that the temperature being pumped does not change in temperature during the transition. Thus, controlling the temperature of stored calibration fluid along with ensuring the temperature of the fluid does not change while the fluid is being pumping to the measuring device, can be both expensive and a difficult process.

There are known examples of varying types of densitometers or the like. For example, U.S. Pat. No. 4,170,128 issued to Kratky et al. (hereafter "KRATKY"), incorporated by reference herein in its entirety, shows a device comprising a U-shaped bending type oscillator connected with a tensioned body responsive to temperature and pressure. However, the above reference has many drawbacks, such as a geometry that requires a large quantity of fluid in order to completely replace a fluid that is initially present in the tube with a second one. Furthermore, it has an internal volume closer to milliliters rather than microliters, and a geometry that it is not optimized to operate at large pressures.

U.S. Pat. No. 7,263,882 issued to Sparks et al. (hereafter "SPARKS"), incorporated by reference herein in its entirety, shows a densitometer relating to chemical concentrations, including those of fuel cell solutions that can be measured by sensing changes in fluid density as a fluid sample flows through a microchannel within a resonating tube of a Coriolis-based microfluidic device. While the SPARKS device discloses the use of Coriolis-based microfluidic devices for sensing the mass flow rates and densities of gases and gas mixtures, many more improvements in the sensitivities of such devices are necessary to fully realize the capabilities of such devices. Further, the SPARKS device discloses an oscillating tube densitometer that is fabricated out of silicon and operates with microliter volumes of sample fluid. The SPARKS device is unable to operate at pressures much above ambient pressures as the vibrating element consists of a thin-walled silicon tube. Moreover, the SPARKs device is not a device operable downhole and is limited to low pressure and low temperature.

U.S. Pat. No. 6,378,364 issued to Pelletier et al. (hereafter "PELLETIER '364"), incorporated by reference herein in its entirety, shows a densitometer for determining fluid properties from vibration frequencies of a sample cavity and a reference cavity. The measurement device of PELLETIER '364 includes a sample flow tube, a reference flow tube, vibration sources and detectors mounted on the tubes, and a measurement module. The sample flow tube receives a flow of sample fluid for characterization. The reference flow tube is filled with a reference fluid having well-characterized properties. The reference flow tube may be pressure balanced to the same pressure as the sample. The measurement module employs the vibration sources to generate vibrations in both tubes. The measurement module combines the signals from the vibration detectors on the tubes to determine properties of the sample fluid, such as density. In particular, to determine the sample fluid density, the measurement module of PELLETIER '364 measures the difference between resonance frequencies of the sample flow tube and the reference flow tube. The density can then be calculated according to a formula. However, the main drawback for the Pelletier device, among other things, is that it requires milliliter-sized volumes as fluid for operation, predominantly discusses measurements with respect to a second tube referred to as a standard, along with being disclosed as a large device. Further, another major drawback of the PELLETIER '364 reference is that it is impractical as well as not commercially viable due to the use of the reference frequency originating from the idea that there will be a second vibrating tube in the tool, filled with a fluid of known properties or a vacuum. Further still, the PELLETIER '364 reference requires the reference frequency due to the structure of the device, e.g., affixing a magnet to the tube and detecting with a pickup coil.

U.S. Pat. No. 6,543,281 B2 issued PELLETIER (hereafter "PELLETIER '281), incorporated by reference herein in its entirety, shows a downhole vibrating tube densitometer. However, the downhole vibrating tube densitometer of PELLETIER '281 has an inner diameter of a tube on the order of 5 mm, leading to a sensor volume of tens of milliliters at a minimum. The PELLETIER '281 has other drawbacks, as mentioned above, utilizes milliliter scale volumes of fluid for operation and requires either the excitation or detection components to be clamped to the tube, thereby decreasing the sensor's sensitivity.

U.S. Published Patent Application US 2008/0156093 to Permuy et al. (hereafter "PERMUY"), is commonly assigned to the same assignee of the present application and incorporated by reference herein in its entirety, and shows a commercialized densitometer (InSitu Density) for flowline applications. The PERMUY devices shows a sensor device based on the use of mechanical elements put into vibration in the fluid to be measured. However, the sensor device of PERMUY requires several milliliters of fluid at a minimum.

Anton Paar is often recognized as the world leader in laboratory vibrating tube densitometers. A recently introduced model is now able to operate at 20,000 psi and at elevated temperatures. However, this device requires milliliters of fluid to measure density. The Anton Paar reference discloses a device that does not incorporate a pressure housing so as to operating in a pressure environment. Further, the Anton Paar reference requires milliliter scale volumes of fluid for operation which is not suitable for below ground environments.

More recently it has been shown that actuation can be achieved by placing part or all of the vibrating tube into a magnetic field and by passing oscillatory current through the tube body itself [J. Herrero-A' lvarez, G. Gonza'lez-Gaitano, and G. Tardajos, Rev. Sci. Instrum. 68, 3835 (1997) and R. F. Chang and M. R. Moldover, Rev. Sci. Instrum. 67, 251 (1996)]. For example, the Chang and Moldover reference (hereafter "CHANG") discloses a vibrating tube design that eliminates electromagnets and appendages attached to tube of the densimeter, and can operate at elevated temperature. CHANG discloses measurements of density of toluene between 298 K (about 900 kg×m−3) and 575 K (about 600 kg×m−3) at pressures below 13.8 MPa. However, there are many drawback to this device since, first there is no disclosed pressure housing, and secondly, the disclosed device would suffer from electrical issues since no electrical isolators or similar like devices have been incorporated.

Therefore, there is a need for methods and devises that overcome the above noted limitations of the prior art. By non-limiting example, devices and methods that can provide a high-accuracy densitometer which is capable of operation under the high temperature, pressure, shock and vibration conditions encountered in a wellbore; which uses a fluid sample volume equal to or less than 100 microliters; and which effectively eliminates the errors associated with the effects of temperature and pressure on the system as well as suppress electrical noise coming from exterior influences positioned exterior to the device.

SUMMARY OF THE INVENTION

According to embodiment of the invention, the invention includes a device for determining one or more properties of at least one fluid sample. The device includes a tube configured to receive the at least one fluid sample wherein the tube is placed in a pressure housing. Further, an excitation source configured to generate vibration of the tube whereby a circulation of an electrical current along a portion of the tube is subjected to at least one magnetic field produced by at least one magnet. Further still, at least one vibration sensor that converts vibrations of the tube into a measurement signal. Finally, a processor that receives the measurement signal determines a resonant frequency from the measurement signal using a frequency measuring device to determine a property of the one or more properties of the at least one sample fluid.

According to aspects of the invention, the tube can be structured and arranged to substantially wrap about an axis of the at least one magnet and bisect a height of the at least one magnet. Further, the at least one magnet is structured and arranged to be approximate to to 30 percent or more of an overall length of the tube filled with the at least one fluid sample. Further still, the tube has a tube geometry shaped from the group consisting of one of at least one bend, two or more bends, a straight tube, one or more shapes or some combination thereof. It is possible the tube vibrates by one of a piezoelectric device, electromagnet actuator or an other vibrating device. Further, the tube vibrates at a frequency characteristic of the one or more properties of the at least one fluid sample. The tube includes at least two ends secured by a holding device such that each end of the tube is electrically isolated from the holding device.

According to aspects of the invention, the holding device can include one or more fastening device such that each fastening device includes an electrically isolated device. The one or more property of the sample fluid determined can be one of density, bubble point, thermodynamic phase, or some combination thereof. Further, a volume of fluid sampled can be one of a microliter, two or more microliters, equal to or less than 100 microliters or some combination thereof. It is possible the one or more fluid sample can be one of a gas, a liquid or some combination thereof. Further, the one or more fluid sample can include one of one or more suspended solid, one or more gel or some combination thereof. Further, the one or more fluid sample can be electrically isolated from one of at least one inlet and at least one outlet. It may be possible for the invention to further comprise of the tube fluidly connected to at least one inlet and at least one outlet, wherein an electrical isolating means electrically isolates the tube from one of the at least one inlet, the at least one outlet, the at least one fluid entering the at least one inlet or the at least one fluid exiting the at least one outlet.

According to aspects of the invention, the device may operable in one of temperatures equal to or less than 350 C or pressures equal to or less than 35,000 psi. Further, the device may be able to determine the one or more properties of the at least one fluid sample while the at least one fluid sample is one of stationary or moving. Further still, the device may further comprise of a filter so as to filter the at least one fluid sample prior to entry of the tube. It is also possible the filter can include a microporous membrane that separates formation fluid from aqueous mud filtrate. For example, using a microporous membrane that separates formation oil from aqueous mud filtrate (see Published Application Serial No. 2006/0008913 that is assigned to the same assignee as the present application).

According to aspects of the invention, the device may operate in one or more mode for vibration. For example, for the U-shape tube, a first mode of the one or more mode for vibration may produce an up and down motion, a second mode of the one or more mode for vibration may produce a side to side motion, a third mode of the one or more mode for vibration may produce a torsional motion. The device can be positioned within a tool such as one of a reservoir tool or a tool for oilfield activities. Further, the pressure housing can seal to protect an exterior of the device from pressure external to the device so as to operate while in a downhole environment. Further still, the pressure housing may seal to protect an exterior of the device from pressure external to the device as well as electrically isolates the device from stray exterior impedances.

According to aspects of the invention, the device can include an electrically isolated holding device that is one of unitary or non-unitary for securing one of the tube, the excitation source, the at least one sensor or some combination thereof. The electrically isolated holding device may include one or more fastening device wherein each fastening device is electrically isolated from one of the tube, the excitation source, the at least one sensor or some combination thereof. Further, the one or more fastening device includes at least one tube fastening device, at least one magnet fastening device, at least one unit fastening device for securing one of the at least one tube fastening device, the at least one magnet fastening device, or at least one other fastening device. It is possible the at least one vibration sensor can be from the group consisting of one of a electrostatic transducer, a piezoelectric transducer, an electric pickup coil, a electromechanical sensor, an induction coil, an optical device or an other vibration sensing device.

According to aspects of the invention, the invention may further comprise at least one sensor for sensing one of temperature and pressure of one of a temperature of the at least one fluid sample, a pressure of the at least one fluid sample, a temperature of the tube or some combination thereof. The at least one sensor or the at least one vibration sensor can be in one of physical contact with the tube or not in physical in contact with the tube. The at least one vibration sensor can be configured to generate vibration of the tube. It is possible the at least one vibration sensor senses a motion of the tube by sensing an electro-magnetic force (emf) or a emf voltage induced along the portion of the tube as the tube moves with respect to the at least one magnetic field. Further, the induced emf or emf voltage is equal to or less than 100 millivolts. Further still, the induced emf or emf voltage is equal to or less than the 100 millivolts as well as requires an amplification by a factor of approximately in the range of 100 to 1,000 before being processed by the processor. It is possible the measurement signal can be an electrical signal.

According to aspects of the invention, at least one magnet can be structured and arranged to be approximate to 35 percent or more of an overall length of the tube filled with the at least one fluid sample. Further, the at least one magnet can be structured and arranged to be approximate to 50 percent or more of an overall length of the tube filled with the at least one fluid sample so as to provide for an increased magnetic field resulting in an increase in accuracy of the device. Further still, the excitation source can be from the group consisting of one of at least one electromagnetic, at least one mechanical resonator, at least one electrostatic device, at least one piezoelectric device, or an other excitation device. The excitation source can be replaced with a different excitation source, wherein the different excitation source is from the group consisting of one of at least one mechanical resonator, electrostatic device, piezoelectric device, an optical device, or an other excitation device. Further, the electrical current can be one of an alternating current or a pulsating current. The excitation source can generate vibration of the tube by alternating a direction of the electrical current with time. Further still, the excitation source is one of physically in contact with the tube or not physically in contact with the tube. The at least one magnet can be shaped as one of a non-curved shape, a box-like shape or a rectangular shape. Further, the tube can have a cavity with an internal cavity volume equal to or less than 100 microliters.

According to aspects of the invention, the processor can be configured to determine one of a vibration frequency response of the tube, a vibration amplitude of the tube, a temperature of the at least one fluid sample, a temperature of the tube, one or more temperatures of the device, one or more pressures of the device, one or more exterior pressures of the device. Further, the processor can be configured to store one or a previously recorded pressure measurement of the at least one fluid, a previously recorded temperature measurement of the at least one fluid, a previously recorded temperature of the tube, one or more previously recorded temperatures and pressure of the device, one or more previously recorded historical data of one or more boreholes or other previously recorded oilfield application data. The processor can also be configured to determine one or more amplitude of the excitation source.

According to embodiments of the invention, the invention includes a device for determining one or more properties of at least one fluid sample in one of a surface environment or a subterranean environment. The device includes a tube configured to receive the at least one fluid sample and an excitation source configured to generate vibration of the tube whereby a circulation of an electrical current along a portion of the tube is subjected to at least one magnetic field produced by at least one magnet. Further, the invention includes an electrical isolating device that results in electrically isolating one of at least one inlet or at least one outlet to the tube so as to suppress electrical conductivity coming from exterior influences positioned exterior to the device. Further, the invention includes at least one vibration sensor that converts vibrations of the tube into a measurement signal. Finally, the invention includes a processor that receives the measurement signal determines a resonant frequency from the measurement signal using a frequency measuring device to determine a property of the one or more properties of the at least one sample fluid.

According to embodiments of the invention, the invention includes a method for measuring one or more properties of at least one fluid sample in a surface environment or a subterranean environment. The method includes (a) receiving at least one fluid sample into a container having an internal fluid volume wherein the container is positioned within a pressure housing; (b) vibrating the container with an excitation source whereby a circulation of an electrical current along a portion of the tube is subjected to at least one magnetic field produced by at least one magnet; (c) sensing the vibration of the container with a vibration sensor wherein the vibration sensor converts vibrations of the tube into a measurement signal that is a container vibration frequency; (d) producing a reference signal from a frequency standard that is independent of the sample container, wherein the reference frequency is recorded by a processor; (e) communicating the container vibration frequency to the processor, wherein the processor determines a frequency ratio between the communicated container vibration frequency and the recorded reference frequency; and (f) converting the frequency ratio to the one or more properties of the at least one sample fluid.

According to aspects of the invention, the invention includes one or more properties of the at least one sample fluid that can be a density measurement of the at least one fluid sample. Further, the container can include one of a tube or a hollow structure capable of holding the at least one fluid sample such that the internal fluid volume is equal to or less than 100 microliters.

According to embodiments of the invention, the invention includes a system for measuring one or more properties such as density of at least one fluid sample in one of a subterranean environment, a surface environment or both. The system includes (a) receiving at least one fluid sample into a hollow structure having an internal fluid volume equal to or less than 950 microliters positioned within a pressure housing; (b) electrically isolating one of at least one inlet, at least one outlet or both to the tube with an electrical isolating device so as to suppress electrical conductivity coming from exterior influences positioned exterior to the device; (c) vibrating the container to obtain a vibration signal having a container vibration frequency and communicating the container vibration frequency to a processor; (d) producing a reference signal from a frequency standard independent of the container, wherein the reference frequency is recorded by the processor; (e) determining a frequency ratio between the recorded reference frequency and the communicated container vibration frequency; (f) converting the frequency ratio to the one or more properties of the at least one sample fluid.

According to embodiments of the invention, the invention includes a method for measuring one or more properties of at least one fluid sample in a subterranean environment wherein the at least one fluid is in one of a single phase or mixed phase. The method includes (a) receiving the at least one fluid sample into a container; (b) vibrating the container to obtain a vibration signal having a container vibration frequency and communicating the container vibration frequency to a processor; (c) producing a reference signal from a frequency standard independent of the container, wherein the reference frequency is recorded by the processor; (d) determining a frequency ratio between the recorded reference frequency and the communicated container vibration frequency; (e) converting the frequency ratio to the one or more properties of the at least one sample fluid.

According to aspects of the invention, the invention includes the one or more properties of the at least one sample fluid that can be a density measurement of the at least one fluid sample.

According to embodiments of the invention, the invention pertains to the measurement of the density of microfluidic volumes of fluids and other fluid properties. The invention describes a rugged densitometer that can operate over a wide range of temperature and pressure. Present oilfield operations include pressures of 30,000 psi or more and temperatures of 200 C or more where such a capability is needed. It is conceived that the application for the invention would include surface and downhole applications. There are several examples that illustrate the utility of an accurate density measurement of microfluidic volume such as at least one embodiment of the invention. Example 1: During the exploration phase the recently drilled open hole well is typically filled with drilling fluids that mix with formation hydrocarbons and provide a source of contamination. In order to obtain representative formation fluids, a formation evaluation tool, such as Schlumberger's Modular Dynamics Tester (MDT) is conveyed into the well via wireline or on drill pipe and the formation fluid is pumped from the porous rock face into the tool. At early time the fluid predominantly consists of mud, but over the course of several hours the contamination level decreases and the fluid becomes more representative of the hydrocarbons in place. This method can be greatly accelerated by using a microporous membrane that separates formation oil from aqueous mud filtrate (see Published Application Serial No. 2006/0008913 that is assigned to the same assignee as the present application), but the rate of fluid separation is significantly less than 1000 microliters/minute, requiring density sensors that can operate with microfluidic volumes. Example 2: Rock core samples containing hydrocarbons are often obtained during the exploration phase and transported to the surface for laboratory analysis. The volume of fluid contained in these cores is typically less than 1 ml. It would be advantageous to be able to displace the fluid in these cores with a second fluid and measure the formation fluid density during this displacement. Again, in order to do so, a density sensor would be required that could make an accurate measurement with microliters of fluid. Example 3: It would be advantageous to run a complete PVT (pressure-volume-temperature) analysis on mere milliliters (or less) of live oil. In particular such small volumes could be rapidly swept or scanned through several temperatures. To do so it would be necessary to measure the density in the single and two phases, and it would be necessary to have a densitometer that could accurately measure the density of a sample with no more than microliters of fluid. Thus, it is noted the above three examples, acknowledge there is a need, among other things, for an accurate densitometer that can simultaneously provide a density measurement with microliters of fluid and simultaneously operate at high pressures and high temperatures as noted above.

Another advantage of at least one embodiment of the invention is that the invention is capable of minimizing the amount of pumped fluid necessary for the densitometer to accurately report the fluid density.

Further features and advantages of the invention will become more readily apparent from the following detailed description when taken in conjunction with the accompanying drawings.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE PREFERRED EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice. Further, like reference numbers and designations in the various drawings indicated like elements.

According to embodiment of the invention, the invention includes a device for determining one or more properties of at least one fluid sample. The device includes a tube configured to receive the at least one fluid sample wherein the tube is placed in a pressure housing. By non-limiting example, the pressure housing may be an oilfield logging tool, oilfield tool or a tool used in either subterranean environments or on the surface. Further, an excitation source configured to generate vibration of the tube whereby a circulation of an electrical current along a portion of the tube is subjected to at least one magnetic field produced by at least one magnet. Further still, at least one vibration sensor that converts vibrations of the tube into a measurement signal. Finally, a processor that receives the measurement signal determines a resonant frequency from the measurement signal using a frequency measuring device to determine a property of the one or more properties of the at least one sample fluid.

Figure 1:
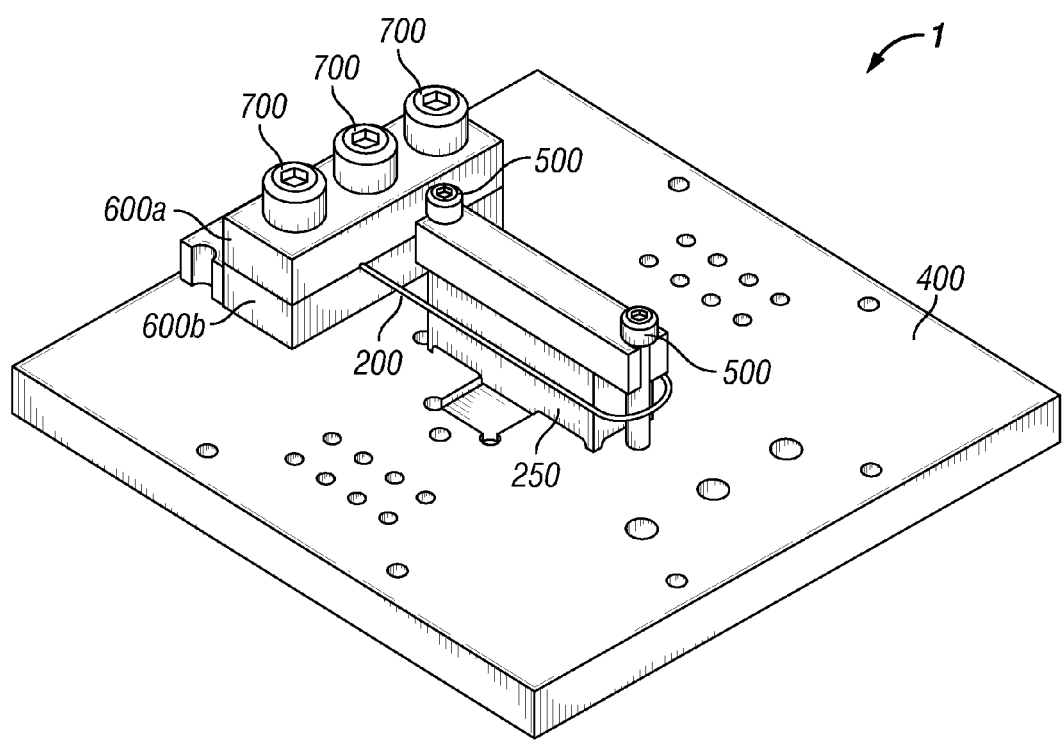
FIG. 1 shows a schematic of the vibrating tube clamped between two plates and wrapped about a permanent magnet such as a SmCo magnet, wherein current is driven through the tube and the resulting Lorentz force provides actuation to drive the tube in a torsional mode and the resulting emf (Faraday's law) is proportional to the tube velocity, according to embodiments of the invention.
Figure 3:
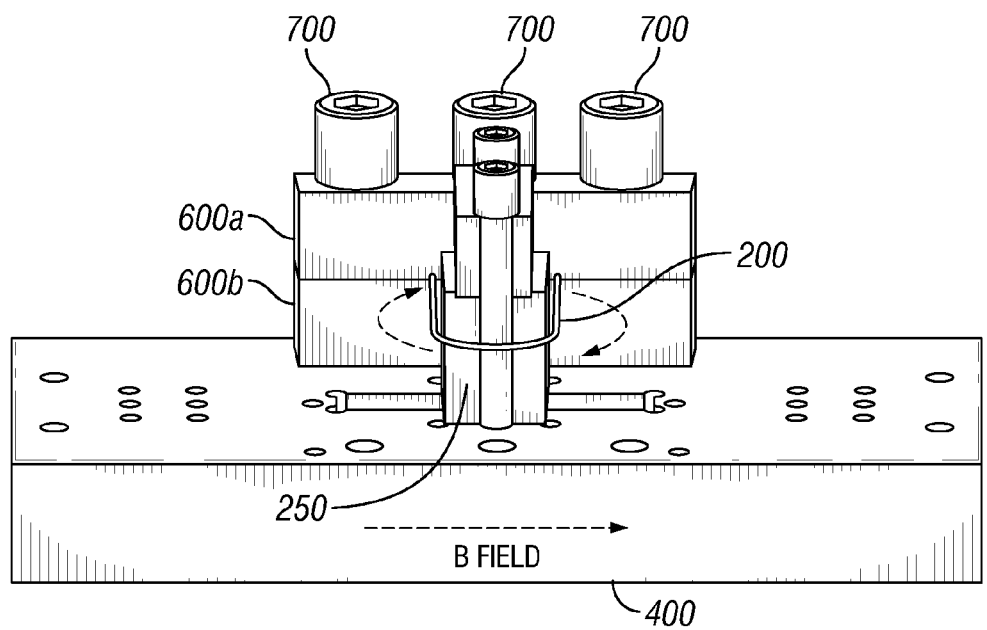
FIG. 3 shows a direction of magnetic field as indicated by the horizontal arrow, the torsional mode's motion is indicated by the curved arrows which are exaggerated for clarity, according to aspects of the invention.

FIG. 1 shows a schematic of the vibrating tube 200 clamped between two plates 600a, 600b and wrapped about a permanent magnet such as a SmCo magnet 250, wherein current is driven through the tube 200 and the resulting Lorentz force provides actuation to drive the tube 200 in a torsional mode and the resulting emf (Faraday's law) is proportional to the tube velocity. It is noted that motion can be monitored by measuring the small emf voltage that develops due to Faraday's law (FIG. 1). The invention is applicable to high pressures up to 15,000 psi or more and high temperatures up to 150° C. or more for determining measurements in a tube having an outer diameter approximate 1/32" along with a fluid sampling volume of less than 20 microliters. It is noted that temperatures in some oilfield applications currently may reach 150 C (it is noted the temperatures could be as high as 350 C) along with pressures of 15,000 psi (it is also noted the pressures could be as high as 35,000 psi). Further, the diameter of the tube can be greater or less and the fluid sampling volume may be up to 1000 micro-liters. Further still, the tubes used in this densitometer, by non-limiting example are made of stainless steel or other related materials having similar properties. However, other types of metals can also be used, for example, titanium or nickel. The outside and inside diameters are approximately 1/32" (0.03125") and approximately 0.020" respectively. A U-shaped tube can either be clamped between two metal plates or brazed into two metal blocks such as copper, where each "leg" of the tube is of approximately length 4.5 cm (FIG. 1), such that the two metal plates or blocks are electrically isolated from the tube by at least one layer of a dielectric material such as mica. The end of the tube can be bent into a half circle of an approximate diameter of 1 cm so as to create an approximate total internal volume of approximately 20 µl (as note above the total internal volume may be approximately up to 1000 µl. It is possible that other shapes of the tube can also contemplated, such as a straight tube or a tube that bent like a cam shaft to take a jog about a magnet. The copper blocks 600a, 600b can be secured to a metal plate 400 by fastening devices 700 such as, screws and then isolated from the plate with thin mica sheets (not shown) or some other similar isolating material. A permanent magnet (SmCo, height 1 cm, length 3 cm, width 0.6 cm) 250 is placed in the interior of the loop and an alternating electrical current is passed through the tube 200. Further, the magnet may be fastened by magnet fastening devices 500, such as screws or some similar magnet fastening means. A typical high pressure fluidic system connects the metal flowline to the electrical ground plane, thereby introducing stray impedances which would alter if not completely ruin the signal used here to measure fluid density. A plastic union can electrically isolate the vibrating tube 200, rendering the vibrating tube electrically floating. However, the plastic union may not be sufficiently reliable under high shock, high temperature, or high pressure environmental conditions, such as downhole conditions. Thus, there may be a need for requiring the development of a high pressure fluidic coupler that can electrically isolated the two coupled tubes, along with being capable of operating in high shock and high temperature device conditions. Electrical connections to the tube 200 are created by either soldering directly or by fastening a wire to each side with a nut and a screw or by some other fastening devices. Alternatively, the wire can be connected directly to the metal block in which the tube is brazed. The magnet 250 can be carefully centered in the loop of the tube 200 such that the loop wraps about the magnet long axis and bisects the magnet height (FIGS. 1 and 3). Fluids are fluidly connected to the tube 200 such that the tube has at least one inlet and at least one outlet.

Figure 2:
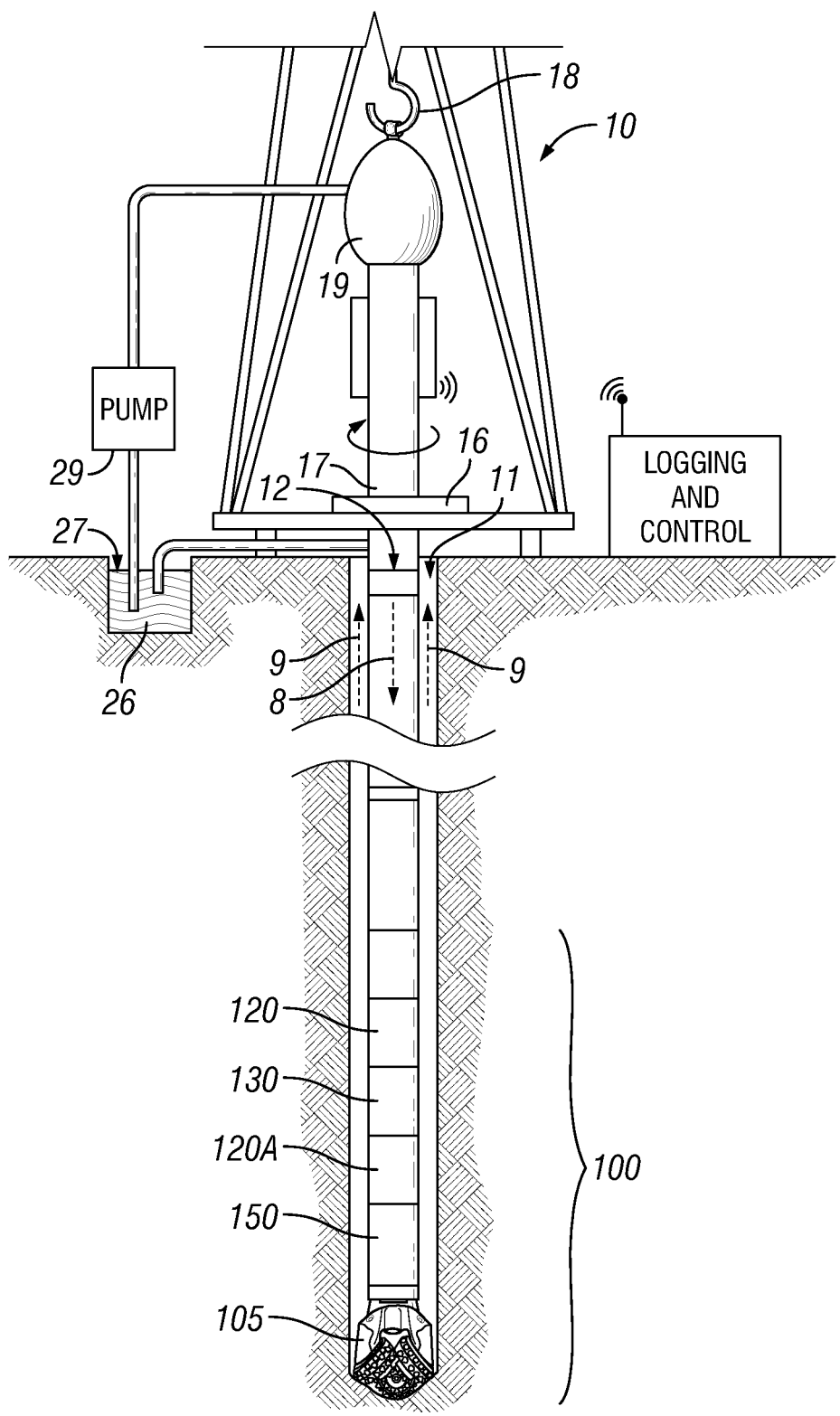
FIG. 2 shows by non-limiting example a schematic diagram of a wellsite system in which at least one pressure housing that may be used according to at least one embodiment of the invention.

FIG. 2 shows by non-limiting example at least one pressure housing that may be used according to at least one embodiment of the invention. In particular, FIG. 2 illustrates a wellsite system in which at least one embodiment of the invention can be employed. The wellsite can be onshore or offshore. In this exemplary system, a borehole 11 is formed in subsurface formations by rotary drilling in a manner that is well known. Embodiments of the invention can also use directional drilling, as will be described hereinafter.

Still referring to FIG. 2, a drill string 12 is suspended within the borehole 11 and has a bottom hole assembly 100 which includes a drill bit 105 at its lower end. The surface system includes platform and derrick assembly 10 positioned over the borehole 11, the assembly 10 including a rotary table 16, kelly 17, hook 18 and rotary swivel 19. The drill string 12 is rotated by the rotary table 16, energized by means not shown, which engages the kelly 17 at the upper end of the drill string. The drill string 12 is suspended from a hook 18, attached to a traveling block (also not shown), through the kelly 17 and a rotary swivel 19 which permits rotation of the drill string relative to the hook. As is well known, a top drive system could alternatively be used.

Also referring to FIG. 2 and according to at least one embodiment of the invention, the surface system further includes drilling fluid or mud 26 stored in a pit 27 formed at the well site. A pump 29 delivers the drilling fluid 26 to the interior of the drill string 12 via a port in the swivel 19, causing the drilling fluid to flow downwardly through the drill string 12 as indicated by the directional arrow 8. The drilling fluid exits the drill string 12 via ports in the drill bit 105, and then circulates upwardly through the annulus region between the outside of the drill string and the wall of the borehole, as indicated by the directional arrows 9. In this well known manner, the drilling fluid lubricates the drill bit 105 and carries formation cuttings up to the surface as it is returned to the pit 27 for recirculation.

FIG. 2 also shows the bottom hole assembly 100 having a logging-while-drilling (LWD) module 120, a measuring-while-drilling (MWD) module 130, a roto-steerable system and motor, and drill bit 105.

FIG. 2 further shows the LWD module 120 being housed in a special type of drill collar, as is known in the art, and can contain one or a plurality of known types of logging tools. It will also be understood that more than one LWD and/or MWD module can be employed, e.g. as represented at 120A. (References, throughout, to a module at the position of 120 can alternatively mean a module at the position of 120A as well.) The LWD module includes capabilities for measuring, processing, and storing information, as well as for communicating with the surface equipment. According to at least one embodiment of the invention, the LWD module can include a fluid sampling device. It is possible that at least one embodiment of the invention can be fluidly connected to the fluid sampling device.

FIG. 2 also discloses the MWD module 130 that can also be housed in a special type of drill collar, as is known in the art, and can contain one or more devices for measuring characteristics of the drill string and drill bit. The MWD tool further includes an apparatus (not shown) for generating electrical power to the downhole system. This may typically include a mud turbine generator powered by the flow of the drilling fluid, it being understood that other power and/or battery systems may be employed. In the present embodiment, the MWD module includes one or more of the following types of measuring devices: a weight-on-bit measuring device, a torque measuring device, a vibration measuring device, a shock measuring device, a stick slip measuring device, a direction measuring device, an inclination measuring device or some other measuring type device.

Figure 2A:
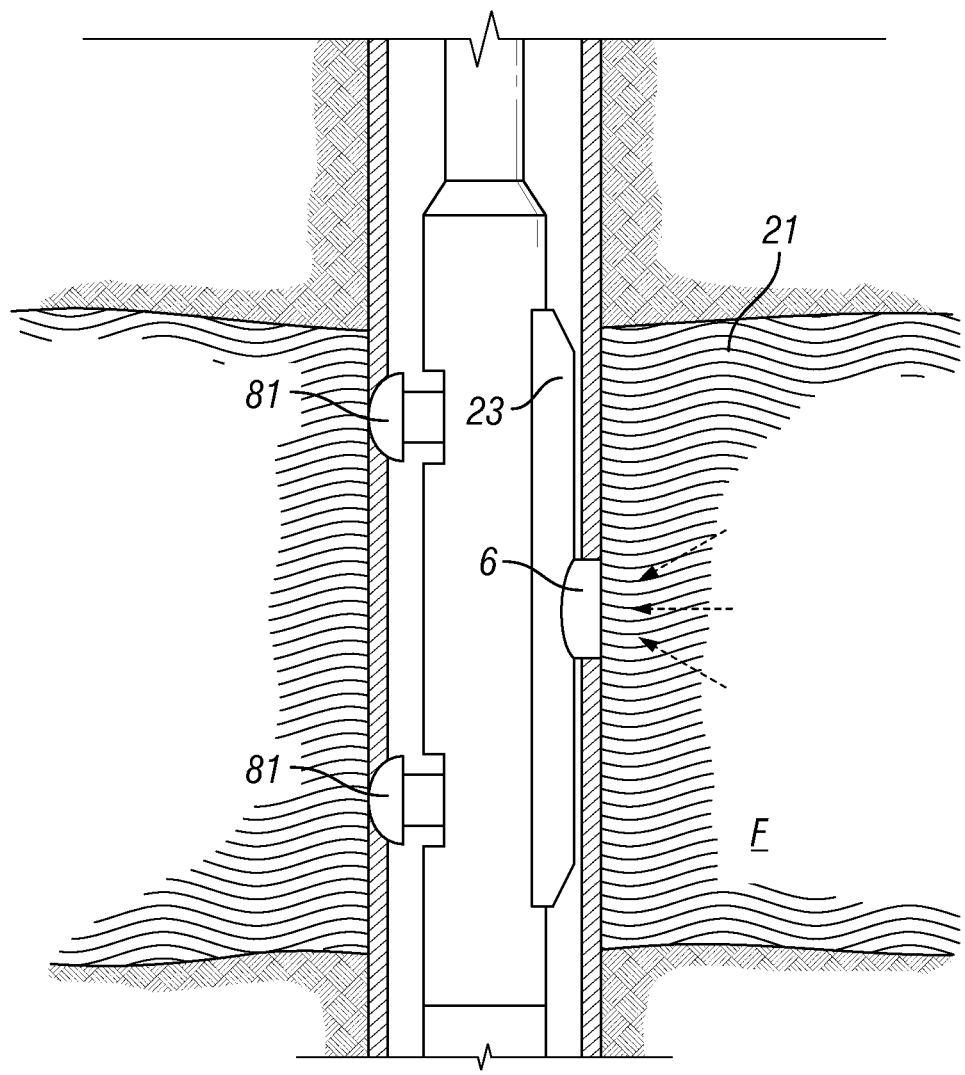
FIG. 2a shows by non-limiting example, a simplified diagram of a sampling-while-drilling logging device of a type described in U.S. Pat. No. 7,114,562 that may be used as a pressure housing, according to at least one embodiment of the invention.

FIG. 2a shows by non-limiting example, a simplified diagram of a sampling-while-drilling logging device of a type described in U.S. Pat. No. 7,114,562, which is incorporated herein by reference, utilized as the LWD tool 120 or part of an LWD tool suite 120A. The LWD tool 120 is provided with a probe 6 for establishing fluid communication with the formation and drawing the fluid 21 into the tool, as indicated by the arrows. The probe may be positioned in a stabilizer blade 23 of the LWD tool and extended therefrom to engage the borehole wall. The stabilizer blade 23 comprises one or more blades that are in contact with the borehole wall. Fluid drawn into the downhole tool using the probe 26 may be measured to determine, for example, pretest and/or pressure parameters. Additionally, the LWD tool 120 may be provided with devices, such as sample chambers, for collecting fluid samples for retrieval at the surface. Backup pistons 81 may also be provided to assist in applying force to push the drilling tool and/or probe against the borehole wall.

FIG. 3 illustrates the vibrating tube 200 that can be driven into oscillation by excitation at its intrinsic resonant frequency with a periodic burst from a current source, for example a current source of 0.5 amps. For example, each burst may consist of ten periods of oscillatory current at the resonant frequency of the tube. The torsional resonance mode can be excited (FIG. 3) due to the oppositely oriented forces on the two legs of the tube 200 that result from the Lorenz force (product of current, path length, and field strength). Due to the high quality factor, the two lower frequency modes comprised of vertical and horizontal motion respectively and are not significantly actuated when the excitation frequency is near that of the torsional mode. The torsional mode (or second harmonic mode) can be chosen for convenience; other modes (as mentioned above, the fundamental vertical mode (diving board mode) and/or the first harmonic (vertical mode or side to side mode) could be more practical for different configurations for the sensor. At least one advantage of using the torsional mode of vibration is that it is not likely to be excited by the vibrations or shocks present in a downhole environment. The amplitude of the resulting emf voltage (resulting from Faraday's law, the temporal change in magnetic flux through closed path) is of magnitude 2 millivolts which is then amplified by a factor of 100 before digitizing with a data acquisition system. (FIG. 4).

Figure 4:
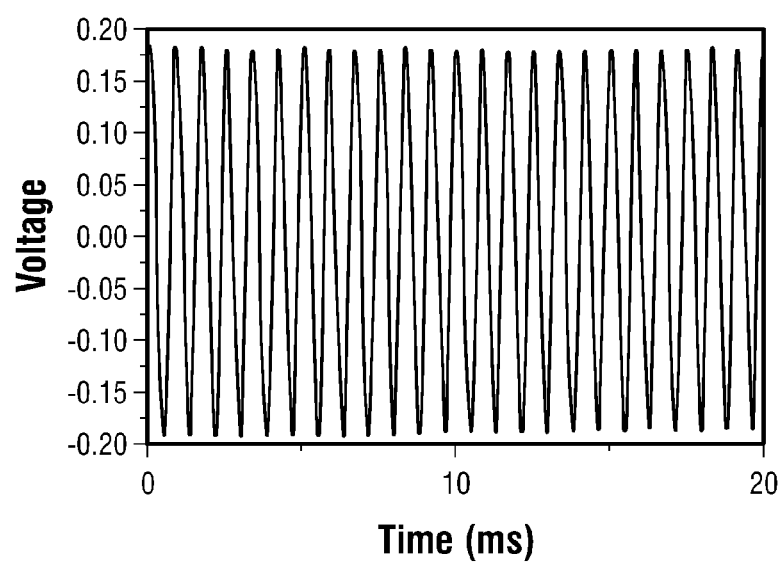
FIG. 4 shows a torsion resonance mode that is excited due to the oppositely oriented forces of the tube wherein the actual amplitude of motion is approximately 10 microns, according to aspects of the invention.

Referring to FIG. 4, it is noted that as the quality factor was several thousand or even higher, very little reduction in amplitude can be noticed during the ringdown. Regression was performed with an exponentially damped sinusoidal function from which the resonant frequency was extracted. The resonant frequency was typically around 1000 Hz and the standard deviation of the 1 second measurement was typically on the order of 0.02 Hz. Other methods are available for measuring the resonant frequency and will be obvious to one skilled in the art. For example, one might sweep an excitation frequency through a wide range of frequencies and determine which excitation frequency produced the largest amplitude. As well, one might count the number of zero-crossings in a given time, which indicates the resonant frequency.

The resonant frequency f of the vibrating tube densitometer can be related to the effective spring constant k and the total mass m as:

$$f = \frac{1}{2\pi}\sqrt{\frac{k}{m}} \qquad \text{Eq. (1)}$$

The total mass m consists of the mass of the tube $m_{tube}$ and the mass of the fluid $\rho V$ where V is the volume of the tube and $\rho$ is the fluid density. Substituting for the mass and solving for the fluid density produces the following equation:

$$\rho = \frac{k}{(2\pi f)^2 V} - \frac{m_{tube}}{V} \qquad \text{Eq. (2)}$$

Equation (Eq. 2) above can be rewritten with two calibration constants A(T,P) and B(T,P) where P and T correspond to pressure and temperature respectively and it is understood that the density and frequency depend upon the same thermodynamic properties.

$$\rho = \frac{A}{f^2} - B \qquad \text{Eq. (3)}$$

Figure 5:
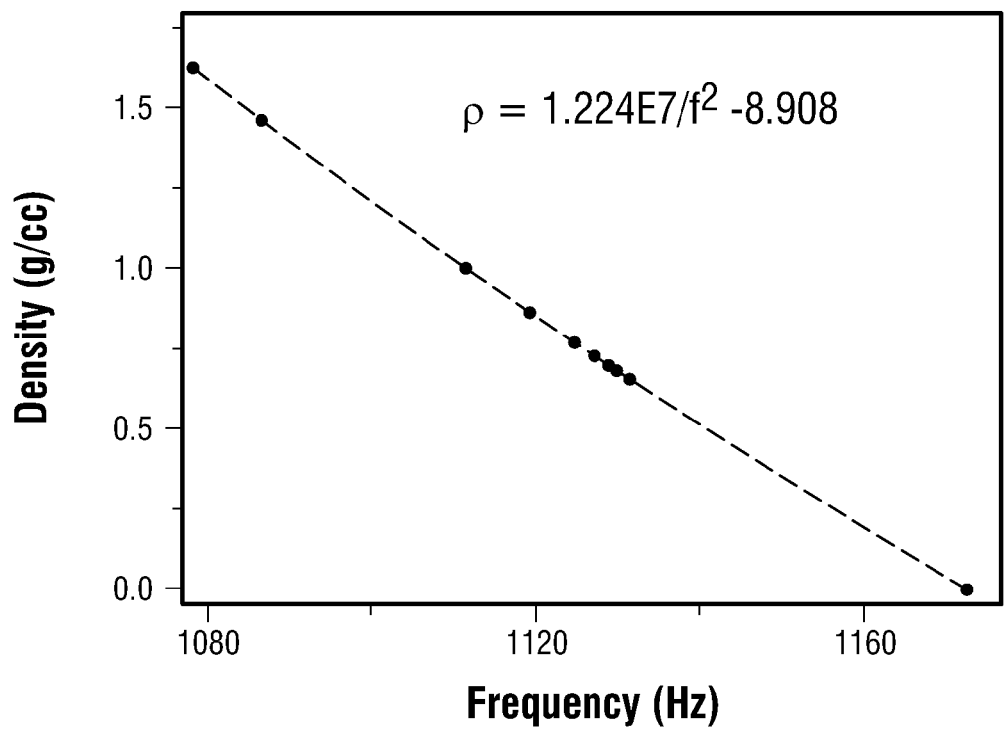
FIG. 5 shows a plot of density versus resonant frequency for the vibrating tube for several fluids at 25 C and ambient pressure, wherein a fit with Equation (3) is superimposed onto the data, according to aspects of the invention.

Referring to FIG. 5, the resonant frequency f of the sensor was first measured with several simple fluids (e.g. hexane, toluene, dichloromethane) at 25 C and at ambient pressure to cover the full density range. The frequency can be seen to decrease as the fluid density increases (FIG. 5) and a fit to the data with equation (Eq. 3) allows for determination of A and B (1.224*107 Hz$^2$ g/cc and 8.908 g/cc respectively). It is noted that a source of error may be speculated to originate from insufficient knowledge of the fluid density in certain cases, but primarily from imprecision in determining the resonant frequency using fitting routines.

Still referring to FIG. 5, there are several existing high pressure and high temperature (HPHT) calibration techniques that can be found in the literature [B. Lagourette, C. Boned, H. Saint-Guirons, P. Xans and H. Zhout, Meas. Sci. Technol. 3, 699 (1992) and M. J. P. Comunas, J-P. Bazile, A.

Baylaucq, C. Boned, J. Chem Eng. Data 53, 986 (2008)], however a calibration procedure for the present invention, by non-limiting example, approximates the spring constant to be independent of pressure. The technique employed requires prior measurement of the resonant frequency of the evacuated vibrating tube over the entire range of temperatures investigated as well as the same for a water-filled vibrating tube over the entire range of temperatures and pressures of the measurement. In practice a sampling of frequency measurements at various (T,P) combinations is made and interpolation is performed for values in between. For simplification we denote the inverse frequency squared when the sensor is filled with water and under vacuum are denoted as ($\Lambda_w$) and ($\Lambda_0$) respectively. The literature values of the density of water ($\rho_w$(T,P)) can be obtained from commonly available sources, such as that provided by NIST. Interpretation resulting from the approximation that k has no pressure dependence results in the following equation for the measurement of the unknown fluid density $\rho$(T,P) [see Lagourette et al. noted above]:

$$\rho(T, P) = \rho_w(T, P) \frac{\Lambda(T, P) - \Lambda_0(T)}{\Lambda_w(T, P) - \Lambda_0(T)} \qquad \text{Eq. (4)}$$

We calibrated the vibrating tube by measuring its frequency at several temperatures ranging from ambient to 150 C when evacuated. In practice, this was done with the vibrating tube filled with air as the density of air would produce an offset that could be absorbed into the calibration. It is noted and acknowledge that the density of air (1.2 kg/m$^3$) introduces a systematic offset to our measurements (0.1% on typical fluid densities), but remembering that the ideal gas law tells us that the density of air will change by less than 25% during our experiments, it is noted that this offset is roughly constant and can be absorbed into the calibration. Further, we measure a difference of 0.08 Hz between the sensor filled with air and that under vacuum, which, not properly accounted for, adds an offset to the measured density of 0.13%. The data were fit with a second order polynomial such that the inverse resonant frequency squared ($\Lambda_0$) could be interpolated at any temperature. Next, the sensor was filled with water and the resonant frequency was measured at several separate pressures for the same temperatures such that the inverse frequency squared $\Lambda_w$ could be calculated for any specified temperature and pressure by interpolation. These two simple sets of automated measurements completed the calibration. Depending upon the pressure and temperature range used, a different and more appropriate calibration method might be employed. The calibration method described here simply describes that which we found most applicable to our application.

Figure 6:
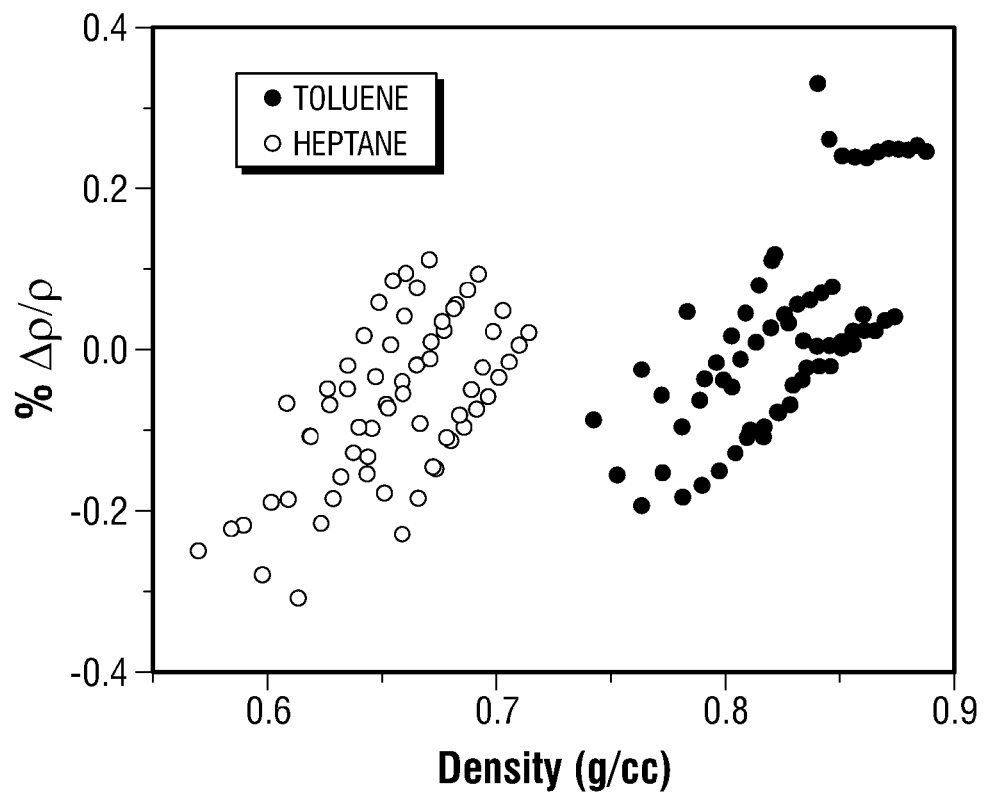
FIG. 6 shows a plot of density discrepancy vs density for heptane (red) and toluene (black) such that these measurements were carried out at temperatures as high as 150 C and pressures as high as 10,000 psi and the accuracy is typically better than +/−0.5 percent, wherein the discrepancy is plotted against density, according to aspects of the invention.

Referring to FIGS. 5 and 6, the sensor was next filled with fluids such as heptane and toluene and a similar set of measurements were undertaken. FIG. 5 shows a discrepancy plot where the majority of the data lie between +/−0.3%, while there are a few outliers with a slightly higher discrepancy. The measurements occurred at temperatures as high as 150 C and pressures as high as 15,000 psi. The average reproducibility of the measurements was about 0.1%. The standard deviation of the 1 second data was approximately 0.03 Hz or better. These data and others were acquired over the course of several months to test the sensor's long-term stability. There appeared to be an upwards drift with respect to time in the resonant frequency thereby biasing to the discrepancy data to be negative. Proper annealing ("burning-in") of the sensor at much higher temperatures has been shown to reduce this to be immeasurably small.

According to embodiments of the invention, the invention can be a highly accurate vibrating tube densitometer fabricated to operate with 20 microliters of fluid or up to 1000 microliters of fluid. The at least one embodiment which discloses miniaturization can accurately detect the motion of the tube without fastening a magnet or pickup coil to the tube, thereby simplifying the design. As noted above, the invention is applicable to high pressures up to 35,000 psi and high temperatures as high as 350 k.

One or more embodiments of the present invention have been described. Nevertheless, it will be understood that various modifications may be made without departing from the spirit and scope of the invention. It is noted that the foregoing examples have been provided merely for the purpose of explanation and are in no way to be construed as limiting of the present invention. While the present invention has been described with reference to an exemplary embodiment, it is understood that the words, which have been used herein, are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A logging tool for determining a property of a fluid sample, the logging tool comprising:
   a pressure housing;
   a fluid sampling device comprising a probe configured to establish fluid communication with a formation and to draw the fluid sample into the logging tool; and
   a device disposed within the pressure housing for determining a property of a fluid sample, the device comprising:
   a tube in fluid communication with the fluid sampling device;
   a filter configured to separate the fluid sample from aqueous mud filtrate prior to entry into the tube;
   a current source configured to pass an electrical current along a portion of the tube;
   at least one magnet configured to apply a magnetic field to the portion of the tube, wherein the magnetic field generates vibration within the tube when the electrical current passes along the portion of the tube, the tube surrounding the at least one magnet along an exterior of the least one magnet;
   a sensor configured to generate a measurement signal by measuring an electromagnetic force voltage that is induced within the tube; and
   a processor that receives the measurement signal and determines the property of the fluid sample using the measurement signal.

2. The logging tool of claim 1, wherein the filter includes a microporous membrane that separates the fluid sample from aqueous mud filtrate.

3. A logging tool for determining a property of a fluid sample, the logging tool comprising:
   a pressure housing;

a fluid sampling device comprising a probe configured to establish fluid communication with a formation and to draw the fluid sample into the logging tool; and a device disposed within the pressure housing for determining a property of a fluid sample, the device comprising:
- a tube in fluid communication with the fluid sampling device;
- a filter configured to separate the fluid sample from aqueous mud filtrate prior to entry into the tube;
- a current source configured to pass an electrical current along a portion of the tube, wherein the portion of the tube that passes the electrical current is electrically isolated from the fluid sampling device;
- at least one magnet configured to apply a magnetic field to the portion of the tube, wherein the magnetic field generates vibration within the tube when the electrical current passes along the portion of the tube;
- a sensor configured to generate a measurement signal by measuring an electromagnetic force voltage that is induced within the tube; and
- a processor that receives the measurement signal and determines the property of the fluid sample using the measurement signal.

4. The device logging tool of claim 3, further comprising:
at least one union for electrically isolating the portion of the tube that passes the electrical current from the fluid sampling device while maintaining fluid communication with the fluid sampling device.

5. The logging tool of claim 1, wherein the tube comprises at least one bend.

6. The device logging tool of claim 1, wherein the tube vibrates at a frequency characteristic of the property of the fluid sample.

7. The device logging tool of claim 1, wherein the property of the fluid sample is density.

8. The device logging tool of claim 1, wherein the fluid sample is less than 100 micro liters.

9. The logging tool of claim 1, wherein the tube has a cavity with an internal cavity volume equal to or less than 1000 micro liters.

10. The logging tool of claim 1, wherein the device determines the property of the fluid sample while the fluid sample is stationary within the tube.

11. The logging tool of claim 1, wherein the logging tool comprises at least one of a sampling-while-drilling tool, a logging-while-drilling tool, and a wireline tool.

12. The logging tool of claim 1, wherein an amplitude of the induced electromagnetic force voltage is equal to or less than 100 millivolts.

13. The logging tool of claim 12, wherein the induced electro-magnetic force voltage is amplified by a factor of 100 to 1,000 before being processed by the processor.

14. The logging tool of claim 1, wherein the processor determines the property of the fluid sample using a temperature measurement and a pressure measurement.

15. The logging tool of claim 14, wherein the temperature measurement is at least one of: a temperature of the tube and a temperature of the fluid sample.

16. The logging tool of claim 14, wherein the pressure measurement is at least one of: a pressure within the tube and a pressure of the fluid sample.

17. The logging tool of claim 1, wherein each end of the tube is secured by a holding device that comprises a plurality of blocks and each end of the tube is clamped between the blocks.

18. The logging tool of claim 17, wherein the holding device comprises an insulating material that insulates each end of the tube from the plurality of blocks.

19. The logging tool of claim 1, wherein the tool is configured to operate at temperatures above 150 ° C. and at pressures above 15,000 pounds per square inch (psi).

20. A logging tool for determining density of a formation fluid, the logging tool comprising:
a pressure housing;
a fluid sampling device comprising a probe configured to establish fluid communication with a formation and to draw the formation fluid into the logging tool; and
a device disposed within the pressure housing for determining density of the formation fluid, the device comprising:
- a tube in fluid communication with the fluid sampling device;
- a microporous membrane that separates the formation fluid from aqueous mud filtrate prior to entry into the tube;
- a current source configured to pass an electrical current along a portion of the tube, wherein the portion of the tube that passes the electrical current is electrically isolated from the fluid sampling device;
- at least one magnet configured to apply a magnetic field to the portion of the tube, wherein the magnetic field generates vibration within the tube when the electrical current passes along the portion of the tube;
- a sensor configured to generate a measurement signal by measuring an electromagnetic force voltage that is induced within the tube; and
- a processor that receives the measurement signal and determines the density of the formation fluid using the measurement signal.

* * * * *